(12) United States Patent
Ozaki (10) Patent No.: US 6,234,794 B1
(45) Date of Patent: *May 22, 2001

(54) ARTICULATOR

(75) Inventor: Kunio Ozaki, Tokyo (JP)

(73) Assignee: Yugen Kaisha A.G.O., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,627

(22) Filed: Oct. 16, 1998

(30) Foreign Application Priority Data

Nov. 7, 1997 (JP) .................................................. 9-305769

(51) Int. Cl.⁷ .................................................. A61C 11/00
(52) U.S. Cl. .................................................. 433/57
(58) Field of Search .......................................... 435/54–65

(56) References Cited

U.S. PATENT DOCUMENTS

| 4,024,640 | * | 5/1977 | Guichet ................................. | 433/57 |
| 4,504,226 | * | 3/1985 | Gordon ................................. | 433/65 X |
| 4,509,919 | * | 4/1985 | Gerbellot-Barrillon ................ | 433/57 |
| 4,687,442 | * | 8/1987 | Wong ................................. | 433/65 X |
| 4,900,254 | * | 2/1990 | Gama ................................. | 433/65 |

| 5,385,470 | * | 1/1995 | Polz ................................. | 433/57 |

FOREIGN PATENT DOCUMENTS

| 6-36812 | 9/1994 | (JP) ................................. | A61C/11/00 |
| 7-95990 | 4/1995 | (JP) ................................. | A61C/11/00 |

* cited by examiner

*Primary Examiner*—Nicholas D. Lucchesi
(74) *Attorney, Agent, or Firm*—Rader, Fishman & Grauer (57) ABSTRACT

It is an object to provide an articulator with which upper and lower jaw models can easily be manufactured, corrected and adjusted so that precise upper and lower jaw models are manufactured, the structure is simplified and operability is improved. An upper jaw model mount, on which an upper jaw model is mounted, is combined with an upper jaw model joining member such that adjustments in the right and left directions can be performed. The upper jaw model joining member is combined with a stand through a slide support mechanism such that right- and left-hand heights can independently be adjusted. A lower jaw model joining member is combined with the stand through a slide guide mechanism such that fore-and-aft directional adjustment can be performed. A lower jaw model mount, having a lower jaw model joining member on which a lower jaw model is mounted, and an incisal table are combined with each other. An incisal pin is combined with the upper jaw model joining member such that a rotational direction and the height can be adjusted. Since adjustment in each direction can independently be performed in each portion, the shape of the jaws of a patient can precisely and easily be reproduced.

6 Claims, 10 Drawing Sheets

ARTICULATOR

BACKGROUND OF THE INVENTION

1. Field of the Invention

The present invention relates to an articulator for use in a process for manufacturing a dental product (hereinafter called "upper and lower jaw models"), such as a preserved dental article, a dental prosthesis or an orthodontics device, for the upper and lower jaw teeth for a dental patient.

2. Related Background Art

Dentures or the like are manufactured by performing a stereoscopic adjustment using an articulator to be adaptable to the characteristic of the shapes of the jaws of each patient so that malocclusion is prevented. In general, the articulator incorporates a lower jaw frame provided with a lower-jaw-model mount to which a lower jaw model is joined; and an upper jaw frame which constitutes a Frankfort plane, which is rotatively combined with the lower jaw frame and which is provided with an upper-jaw-model mount to which an upper jaw model is joined. The articulator incorporates an incisal pin which is provided for the upper jaw frame and arranged to be brought into contact with an incisal table provided for the lower jaw frame so that the vertical positions of occlusion planes of the lower jaw model and the upper jaw model are determined.

The articulator is arranged to accurately reproduce complicated anatomical motions of jaws so as to manufacture a further accurate upper and lower jaw models, such as a dentures. Therefore, the articulator is structured such that a variety of complicated adjustment mechanisms are provided for the above-mentioned basic elements.

For example, in Japanese Patent Laid-Open No. 7-95990, an articulator has been disclosed, in which a lower-jaw-model support frame, to which a lower jaw model is joined, and an upper-jaw-model support frame, to which an upper jaw model is joined, can be adjusted in terms of the relative rotational directions, combination of angles in a vertical direction and the fore-and-aft positions. Therefore, the upper- and lower-jaw-model support frames are supported by upper and lower frames through slide mechanisms and spherical joints. Moreover, in Japanese Utility-Model Publication No. 6-36812 having a title "ARTICULATOR", an articulator has been disclosed which has a structure that upper and lower frames are slidably supported by a stand in fore-and-aft directions. Moreover, an upper-jaw-model support frame, to which the upper jaw model is joined, and a lower-jaw-model support frame, to which the lower jaw model is joined, are rotatively supported by upper and lower frames.

As described above, in order to accurately reproduce complicated motions of the jaws, the conventional articulator must have a variety of adjustment mechanisms. Therefore, the conventional articulator has problems in that the number of required elements cannot be decreased, the overall structure becomes too complicated, the overall cost cannot be reduced and the operability and durability deteriorate. Since the conventional articulator is a costly apparatus, a multiplicity of the articulators cannot easily be provided for a dental clinic or the like. Therefore, whenever upper and lower jaw models are manufactured for each patient, the upper and lower jaw models must be changed. Thus, the efficiency deteriorates excessively.

In general, the articulator is used to manufacture dentures or the like by using upper and lower jaw models and plaster. When, for example, the dentures are manufactured, water is used in a large quantity in a cleaning process. Therefore, the articulator must be manufactured in such a manner that powder and broken pieces of plaster and the like can easily be removed. Moreover, rust prevention is required. Since the conventional articulator is provided with a variety of complicated adjustment mechanisms, there arises a problem in that powder and broken pieces of plaster introduced into the adjustment mechanism cannot easily be removed, a breakdown takes place and rust is formed.

For example, the articulator disclosed in Japanese Patent Laid-Open No. 7-95990 has the structure that each of the support frames to which the upper and lower jaw models are joined is supported by the frame through the spherical joint. Thus, there is apprehension that powder and broken pieces of plaster will be introduced into the spherical joint and thus each support frame cannot smoothly be operated for performing the adjustment process. What is worse, the relative positioning accuracy deteriorates in the foregoing case. The articulator disclosed in Japanese Utility-Model Publication No. 6-36812 has a problem in that the upper and lower frames cannot smoothly be slid with respect to the stand. Since the upper jaw model serving as a reference is moved when the upper and lower jaw models are manufactured, the reference position cannot be defined. Thus, there arises a problem in that the adjustment operation cannot easily be performed.

It is preferable that the articulator has satisfactory operability and ease of maintenance as compared with a structure having a multiplicity of functions. Moreover, excellent durability and cost reduction have been required. That is, the articulator is not required to have functions which are capable of completely reproducing the complicated motions of the jaws. The upper and lower jaw models are simply required to be manufactured such that the occlusion of a patient can satisfactorily be reproduced. Moreover, the articulator only needs to perform those functions which enable correction and adjustment of the occlusion.

The articulate ligamentum positioned between the maxilla and the mandible is shifted together with the mandible when the lower jaw is moved. Therefore, correction or adjustment of the upper and lower jaw models is performed in consideration of the above-mentioned shift by using the articulator. The inventor of the present invention has studied the shift of the articulate ligamentum. As a result, attention is paid to a fact that the main movement of the lower jaw of a major portion of patients is a substantially rotational motion in the horizontal direction with respect to a Frankfort plane such that substantially the center of the lower jaw is the center of the rotational motion.

Therefore, the articulator must have a function which is able to rotate the lower jaw model in the horizontal direction around the center of the lower-jaw-model support frame, to which the lower jaw model is joined, the lower jaw model being rotated with respect to the Frankfort plane of the upper frame. As a matter of course, the articulator is provided with a function for rotating the upper frame with respect to the lower frame and a function for adjusting the height of occlusion or occlusion in the fore-and-aft direction to easily manufacture the articulator.

Since the articulator is frequently manipulated when the upper and lower jaw models are manufactured or when correction or adjustment is performed, the articulator must easily be held and handled. Since the conventional articulator has the function for accurately reproducing the motion of the jaws as an important function, the conventional articulator is provided with complicated mechanisms.

Therefore, the conventional articulator cannot easily be held and handled and the weight reduction cannot easily be realized. As a result, there arises a problem in that the operability of the conventional articulator is unsatisfactory.

SUMMARY OF THE INVENTION

Accordingly, an object of the present invention is to provide an articulator which is capable of overcoming the problems experienced with the conventional articulator, which is able to easily manufacture, correct and adjust upper and lower jaw models, with which precise upper and lower jaw models can be obtained, which has a simple structure, which can easily be maintained and operated and the cost of which can be reduced.

To achieve the above-mentioned object, according to one aspect of the present invention, there is provided an articulator comprising upper and lower jaw frames. The lower jaw frame incorporates: a stand constituted by a pair of columnar portions and a connection portion for connecting the columnar portions to each other such that the columnar portions and the connection portion are integrally formed; a lower jaw model joining member combined such that the base portion of the lower jaw model joining member is slidable in a horizontal direction with respect to the connection portion of the stand; a lower jaw model mount which is joined to a joining portion at the center of a main surface of the lower jaw model joining member and which has a main surface on which a lower jaw model is mounted; and an incisal table provided for another end of the lower jaw model joining member. The upper jaw frame incorporates: an upper jaw model joining member having the base, the side portions of which are supported by a rotation support mechanism and a slide support mechanism such that the side portions are rotative and slidable with respect to each columnar portion of the stand; an upper jaw model mount which corresponds to the incisal table of the lower jaw model mount, which is joined to a joining portion formed at the center of a main surface of the upper jaw model joining member constituting a Frankfort plane and which is movable in a horizontal direction perpendicular to a sliding direction of the lower jaw model joining member; and an incisal pin joined to a leading end of the upper jaw model joining member through a support mechanism which is slidably supported such that oscillations are permitted.

The articulator has a structure that each element of the upper jaw frame and lower jaw frame is chamfered so that the outer edge of each element is formed into a moderate circular arc shape. The articulator is provided with a model joining adjustment apparatus incorporating a base secured to the main surface of the lower jaw model joining member and an upper-jaw-model joining reference frame having a height which can be adjusted with respect to the base and an angle which is made from the main surface of the lower jaw model joining member and which is adjustable. The upper jaw model is mounted on the upper jaw model joining member provided for the upper jaw model joining member which constitutes the upper jaw frame.

In the articulator having the above-mentioned structure and according to the present invention, the lower jaw model is mounted on the lower jaw model mount. Moreover, the upper jaw model is mounted on the upper jaw model mount. In the articulator, the upper jaw model joining member is slid with respect to the right and left stands so that the positions of the right and left jaw joints of a patient are accurately reproduced. Thus, the right- and left-hand heights of the lower jaw model and the upper jaw model can be adjusted. In the articulator, the upper jaw model mount is slid with respect to the upper jaw model joining member so that the right- and left-hand occlusion states of a patient are accurately reproduced. Thus, the right- and left-hand occlusion states of the lower jaw model and the upper jaw model are adjusted. The articulator has the structure that adjustment is performed such that the incisal pin is abutted against the central portion of the incisal table. Thus, the distance between the lower jaw frame and the upper jaw frame is set to correspond to the distance between the upper jaw and the lower jaw of the patient so that the height of the Frankfort plane is reproduced. The articulator has the structure that the incisal pin, which has a deviated center when the right- and left-hand heights of the upper jaw model joining member with respect to the stand are adjusted is adjusted because the incisal pin is rotated with respect to the upper jaw model joining member. The articulator according to the present invention and having the structure in which each portion can be adjusted is able to accurately reproduce the movement of the jaws of a patient. Therefore, upper and lower jaw models can precisely be corrected and adjusted.

The articulator is provided with the model joining adjustment apparatus which is joined to the lower jaw model joining apparatus. In a state where the angle and height of the upper-jaw-model joining reference frame with respect to the Frankfort plane have been adjusted, the upper jaw model is temporarily joined. The articulator has the structure that the upper jaw model, which serves as a reference when the upper and lower jaw models are manufactured, is precisely mounted on the upper jaw model mount through the model joining adjustment apparatus.

Other objects, features and advantages of the invention will be evident from the following detailed description of the preferred embodiments described in conjunction with the attached drawings.

DESCRIPTION OF THE PREFERRED EMBODIMENTS

Figure 1:
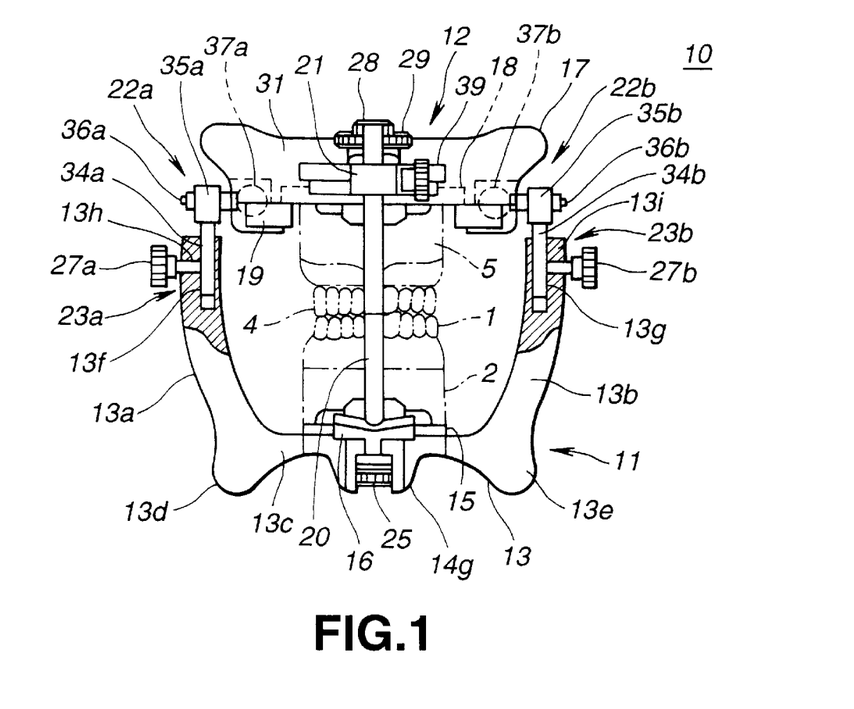
FIG. 1 is a partially-cut front view showing an embodiment of an articulator according to the present invention.
Figure 2:
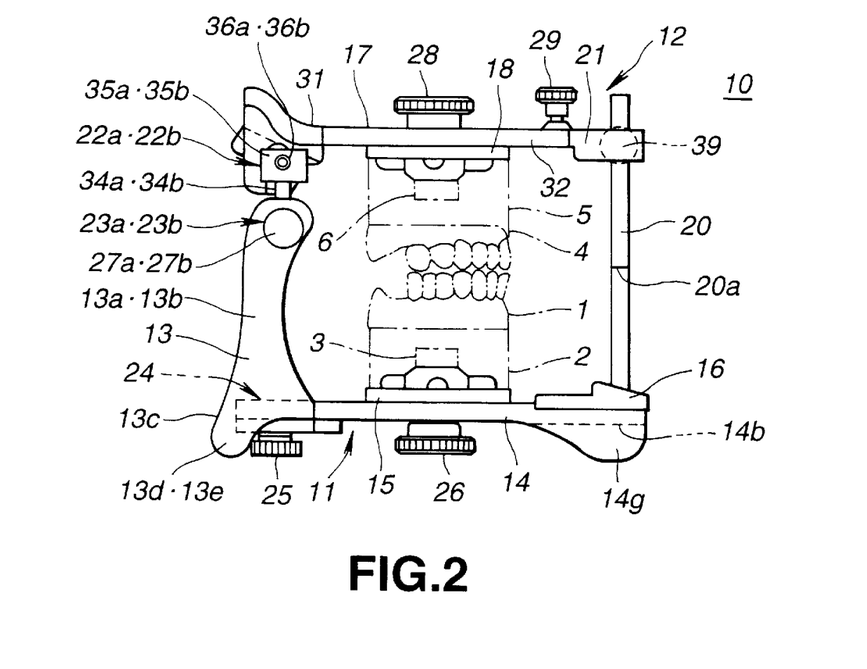
FIG. 2 is a side view showing the articulator according to the present invention.
Figure 3:
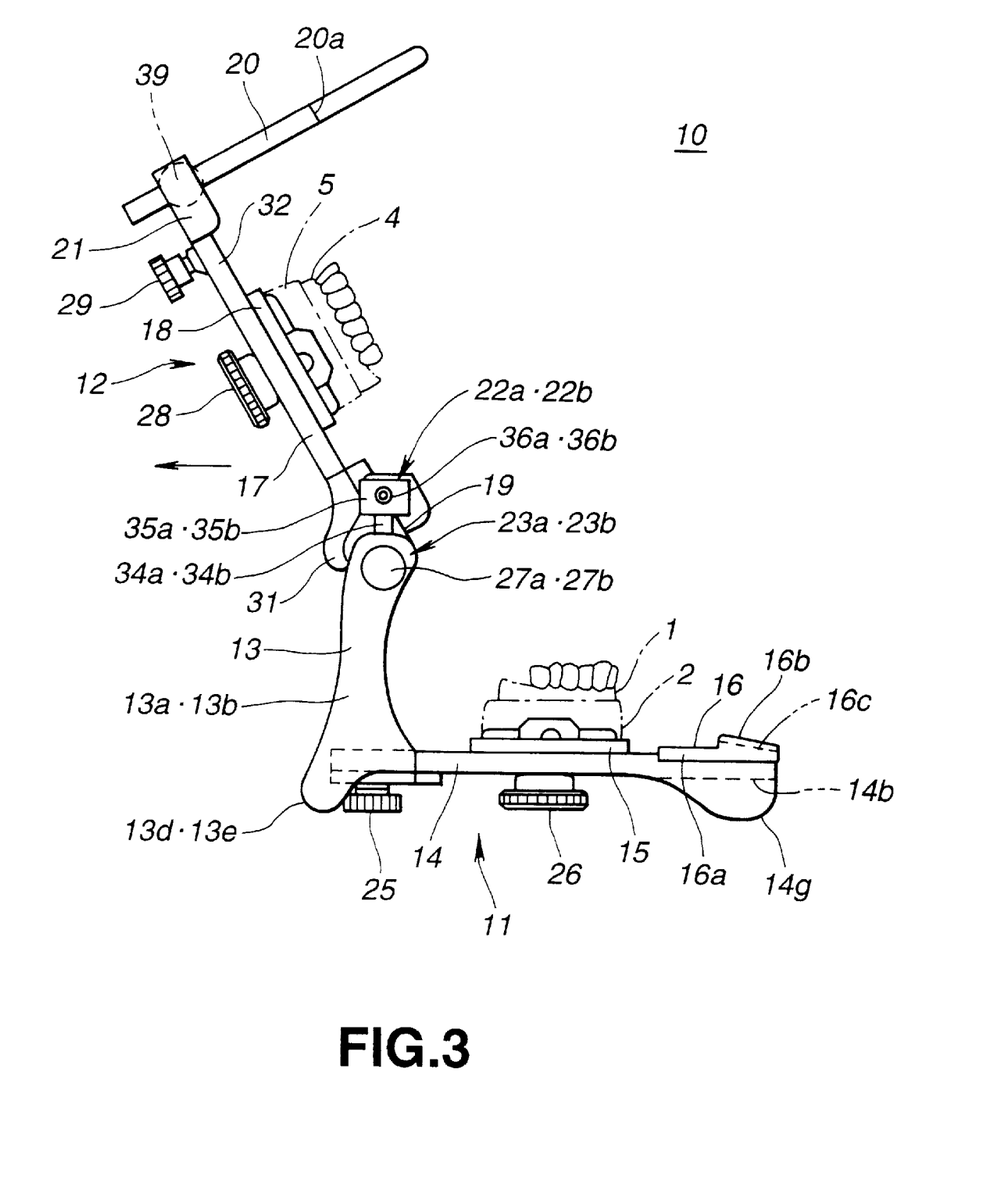
FIG. 3 is a side view showing a state in which an upper jaw model joining member has been rotated.

An embodiment of the present invention will now be described with reference to the drawings. As shown in FIGS. 1 to 3, an articulator 10 incorporates an assembled lower jaw frame 11, to which a lower jaw model 1 is joined and which has an L-shape side cross section. Moreover, the articulator 10 incorporates an upper jaw frame 12 which is combined with the lower jaw frame 11 rotatively with respect to the lower jaw frame 11 and to which an upper jaw model 4 is joined. The lower jaw frame 11 incorporates a stand 13, a lower jaw model joining member 14, a lower jaw model mount 15 and an incisal table 16. The upper jaw frame 12 incorporates an upper jaw model joining member 17, an upper jaw model mount 18, a leaf spring 19, an incisal pin 20 and an incisal pin holder 21.

Note that the descriptions "upper", "lower", "right" and "left" in this specification are those which are used with reference to FIG. 1. The description "fore-and-aft" is a description which is used with reference to FIG. 2 such that the left-hand direction is a "fore" direction and a right-hand direction is an "aft" direction.

The articulator 10 has a structure that the upper jaw frame 12 is combined with the lower jaw frame 11 by dint of a rotation support mechanism 22 and a slide support mechanism 23 to be described later. The upper jaw frame 12 is able to rotate with respect to the lower jaw frame 11 and slide in the direction of the height. The upper jaw frame 12 of the articulator 10 is detachable with respect to the lower jaw frame 11 through the rotation support mechanism 22. The articulator 10 incorporates the lower jaw model joining member 14 which is, by a slide guide mechanism 24 to be described later, slidable with respect to a stand 13 which constitutes the lower jaw frame 11.

The articulator 10 incorporates a first fixing screw 25 for securing, to a predetermined position, the lower jaw model joining member 14, which can be adjusted in the right and left directions in FIG. 2, with respect to the stand 13 by the slide guide mechanism 24. Moreover, the articulator 10 incorporates a second fixing screw 26 for securing the lower jaw model mount 15 with respect to the lower jaw model joining member 14. The articulator 10 incorporates a right and left third fixing screws 27 (27a and 27b) forming a pair and setting and securing the upper jaw model joining member 17, the height of which can be adjusted with respect to the stand 13 by the slide support mechanism 23. The articulator 10 incorporates a fourth fixing screw 28 for securing the upper jaw model mount 18 with respect to the upper jaw model joining member 17. The articulator 10 incorporates a fifth fixing screw 29 for securing the incisal pin holder 21 with respect to the upper jaw model joining member 17.

As shown in FIG. 2, the articulator 10 has the structure that the lower jaw frame 11 and the upper jaw frame 12 are combined with each other such that the cross section is formed into a U-shape facing side. Thus, the upper and lower jaw models 1 and 4 are manufactured. In the above-mentioned state of the articulator 10, the lower end of the incisal pin 20 adjacent to the upper jaw frame 12 is brought into contact with the incisal table 16 adjacent to the lower jaw frame 11. Thus, the distance between the lower jaw frame 11 and the upper jaw frame 12 is made to correspond to a Frankfort plane. As shown in FIG. 3, when the upper jaw frame 12 has been rotated with respect to the lower jaw frame 11 if necessary, the movement of the articulator 10 is stopped at a position at which the upper jaw frame 12 has been rotated by 90 degree or more. As described later, the articulator 10 has a structure that the upper jaw frame 12 can be removed from the lower jaw frame 11 through the rotation support mechanism 22.

The stand 13 is made of, for example, a metal material, e.g. aluminum die-cast or stainless steel. The stand 13 is composed of a pair of columnar portions 13a and 13b and a connection portion 13c for integrally connecting the columnar portions 13a and 13b with each other at a position in the lower portion of the stand 13. The stand 13 has a U-like shape. As shown in FIGS. 1 and 2, the stand 13 has the connection portion 13c formed such that the two side portions of the bottom surface of the connection portion 13c are downwards expanded to form circular-arc projections. Thus, seating members 13d and 13e are formed. To manufacture the lower jaw model 1 and the upper jaw model 4 to image the jaws, the stand 13 has a structure that the side shapes of the columnar portions 13a and 13b are formed into moderate circular arc shapes corresponding to the degree of extension of each pyramid, that is, the shapes of the gills. The stand 13 is provided with a relatively large curvature over the external edges so that the stand 13 is easily held.

Figure 4:
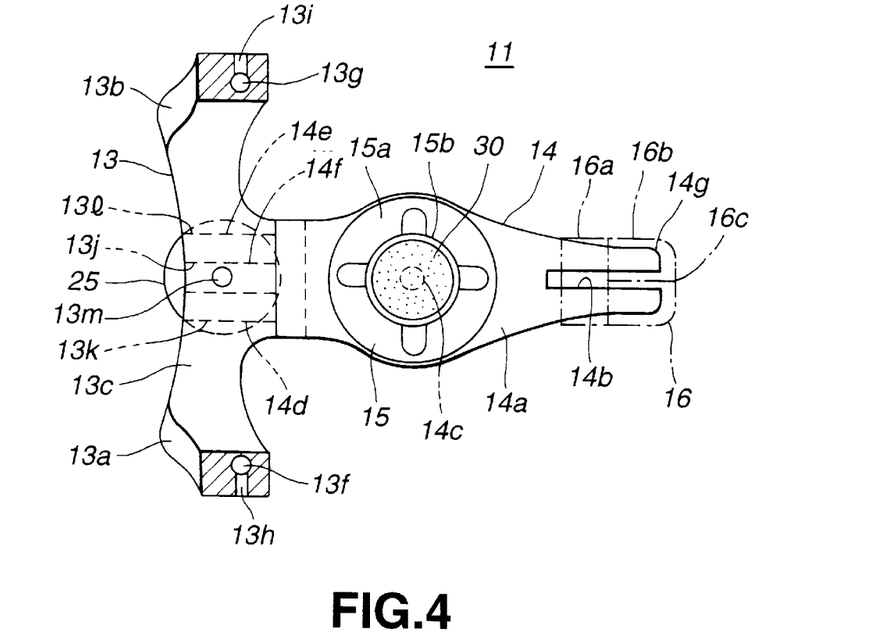
FIG. 4 is a partially-cut plan view showing the structure of a stand and a lower jaw model joining member constituting the articulator.
Figure 5:
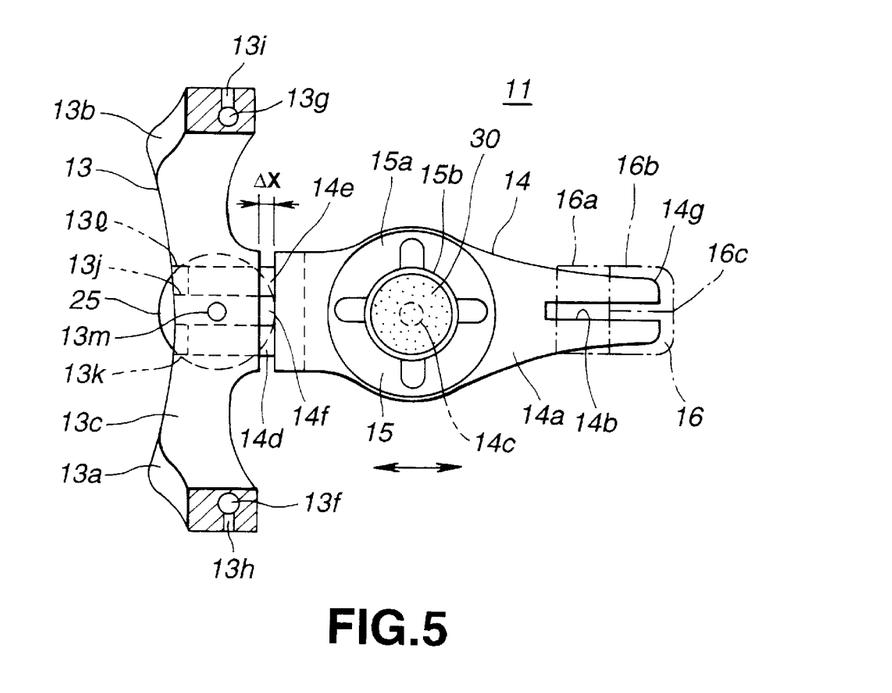
FIG. 5 is a partially-cut plan view showing a state of the articulator in which the lower jaw model joining member has been pulled forwards with respect to the stand.
Figure 6:
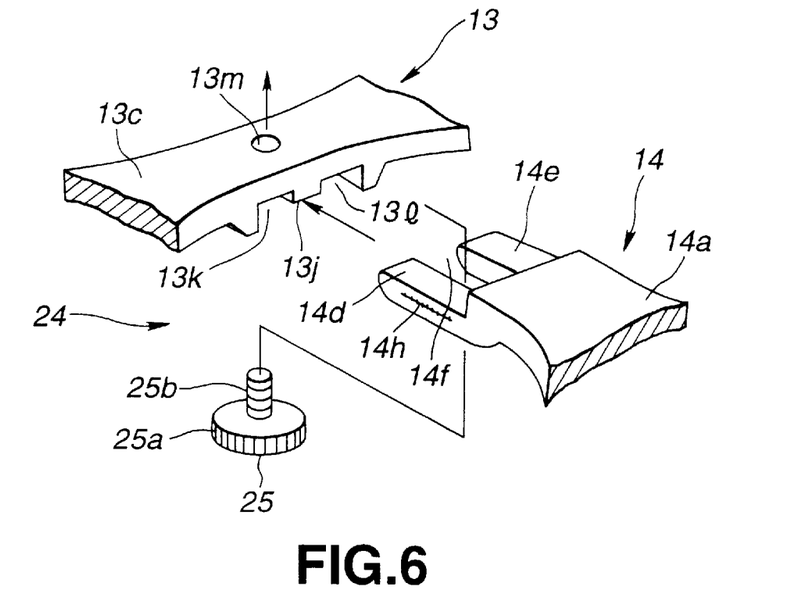
FIG. 6 is an exploded perspective view showing a slide guide mechanism of the articulator which is disposed between the stand and the lower jaw model joining member.

The columnar portions 13a and 13b of the stand 13 have vertical-directional slide guide openings 13f and 13g which constitute a rotation support mechanism 22 to be described later such that the slide guide openings 13f and 13g are opened in the upper surface of the columnar portions 13a and 13b, as shown in FIGS. 1, 4 and 5. The columnar portions 13a and 13b are provided with thread holes 13h and 13i which are allowed to communicate with the slide guide openings 13f and 13g, the thread holes 13h and 13i being opened in the side surfaces of the columnar portions 13a and 13b. A portion for constituting the slide guide mechanism 24 is provided for the stand 13, the slide guide mechanism 24 being positioned in the central portion of the bottom surface of the connection portion 13c so as to slidably support the lower jaw model joining member 14 to be described later, as shown in FIG. 6. The slide guide mechanism 24 adjacent to the stand 13 incorporates a slide guide projection 13j for the fore-and-aft direction, a pair of slide guide grooves 13k and 13l formed along the slide guide projection 13j and a thread hole 13m which is allowed to communicate with the slide guide projection 13j.

The lower jaw model joining member 14 is made of, for example, aluminum die-cast or stainless steel and formed into a plate-like shape. The central portion of the lower jaw model joining member 14 has a central portion which is sidewards expanded into a circular arc shape so as to serve as a mount joining portion 14a to which the lower jaw model mount 15, to be described later is joined. The leading end of the lower jaw model joining member 14 has a table joining groove 14b to which the incisal table 16 to be described later is joined. Moreover, a portion of the slide guide mechanism 24 is provided for the base portion of the lower jaw model joining member 14. The mount joining portion 14a has a thread hole 14c which is formed at the central portion thereof and to which the lower jaw model mount 15 to be described later is joined.

As shown in FIG. 6, the slide guide mechanism 24 adjacent to the lower jaw model joining member 14 incorporates a pair of slide projections 14d and 14e integrally formed from the rear end of the mount joining portion 14a such that the portion corresponding to the thickness of the connection portion 13c of the stand 13 is cut. Moreover, the slide guide mechanism 24 incorporates a slide guide groove 14f formed in the fore-and-aft direction between the slide projections 14d and 14e. The width of each of the slide projections 14d and 14e is substantially the same as that of the slide guide grooves 13k and 13l adjacent to the stand 13. The width of the slide guide groove 14f is substantially the same as that of the slide guide projection 13j of the stand 13. Note that the lower jaw model joining member 14 has a mount 14g in the form of a circular arc projection expanded in the bottom surface of the leading end of the lower jaw model joining member 14. The other slide projection 14d has an index 14h formed on the side surface thereof, as shown in FIG. 6. The index 14h indicates an amount of sliding when the lower jaw model joining member 14 is slid with respect to the stand 13 as described later.

In the slide guide mechanism 24 having the above-mentioned elements, the slide projections 14d and 14e are engaged to the slide guide grooves 13k and 13l. Moreover, the slide guide projection 13j is engaged to the slide guide groove 14f. Thus, the base portion of the lower jaw model joining member 14 is slidably and in a cantilever manner supported with respect to the connection portion 13c of the stand 13. When the first fixing screw 25 is tightened, the lower jaw model joining member 14 is secured to a predetermined position of the stand 13.

As shown in FIG. 6, the first fixing screw 25 incorporates a disc-shape operation portion 25a and a thread portion 25b formed in the central portion of the operation portion 25a. The first fixing screw 25 is screwed in from the bottom upper jaw of the lower jaw model joining member 14 through the slide guide groove 14f such that the thread portion 25b is received in the thread hole 13m of the stand 13. The inner surface of the operation portion 25a of the first fixing screw 25 presses the slide projections 14d and 14e against the inner surfaces of the slide guide grooves 13k and 13l so that the lower jaw model joining member 14 is secured to a predetermined position of the connection portion 13c of the stand 13.

In the articulator 10, the lower jaw model joining member 14 is forwards moved from a state shown in FIG. 4 with respect to the stand 13 through the slide guide mechanism 24 so as to be adjusted within the range defined by the slide guide groove 14f. In a state in which the first fixing screw 25 has been loosened, the lower jaw model joining member 14 of the articulator 10 is forwards slid with respect to the stand 13. When the first fixing screw 25 of the articulator 10 is tightened in a state in which the lower jaw model joining member 14 has been slid in a quantity of discharge Dx with reference to the index 14h as shown in FIG. 5, the lower jaw model joining member 14 is secured to the stand 13. Thus, the articulator 10 is brought to a state in which the fore-and-aft directional occlusion of the patient can be reproduced. Thus, the state of occlusion between the lower jaw model 1 and the upper jaw model 4 in the fore-and-aft direction can be adjusted.

The slide guide mechanism 24 may have another structure in which the slide guide projection 13j and the slide guide grooves 13k and 13l of the stand 13 are provided for the lower jaw model joining member 14. Moreover, the slide projections 14d and 14e and the slide guide groove 14f of the lower jaw model joining member 14 are provided for the stand 13. In addition, the slide guide projection 13j and the slide guide grooves 13k and 13l of the stand 13 may be constituted by one slide guide projection and a slide guide groove in the form of an elongated hole.

Figure 7:
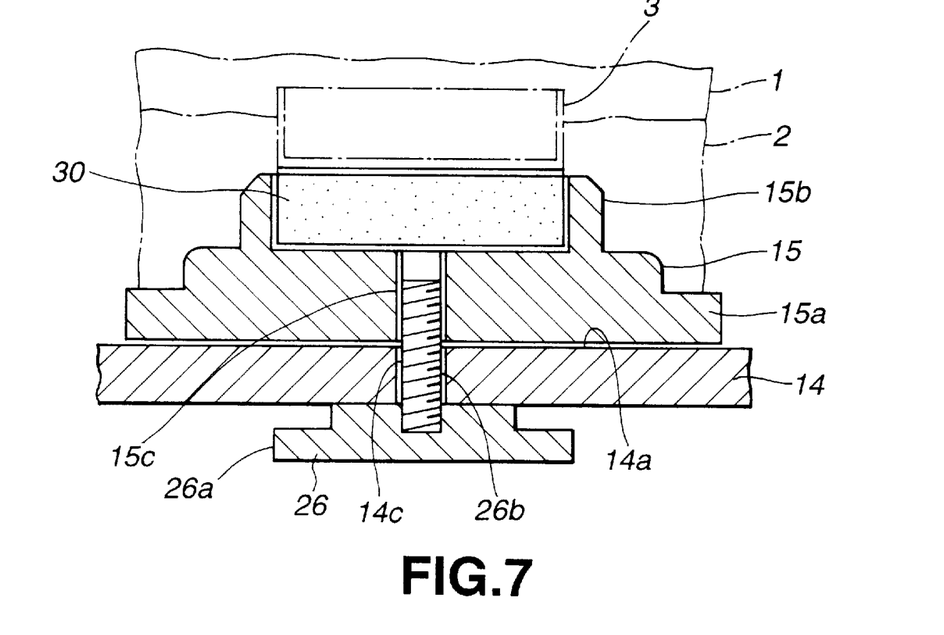
FIG. 7 is a vertical cross sectional view showing an essential portion of a structure formed by combining the lower jaw model joining member and a lower jaw model mount which constitute the articulator.

The lower jaw model mount 15 is joined to the upper surface of the mount joining portion 14a of the lower jaw model joining member 14. As shown in FIGS. 1 to 3, the lower jaw model 1 is mounted on the lower jaw model mount 15 by mounting plaster 2 and a metal plate 3, as shown in FIGS. 1 to 3. As shown in FIG. 7, the lower jaw model mount 15 incorporates a base 15a formed into a disc-like shape and an annular projection 15b integrally projecting over the main surface of the base 15a. The base 15a has a thread hole 15c formed at the center thereof such that the thread hole 15c penetrates the inside portion of the annular projection 15b. A disc-shape magnet plate 30 for magnetically chucking the metal plate 3 of the lower jaw model 1 is joined to the inside portion of the annular projection 15b.

As described above, the lower jaw model mount 15 is secured to the upper surface of the mount joining portion 14a of the lower jaw model joining member 14 by the second fixing screw 26. As shown in FIG. 7, the second fixing screw 26 incorporates a disc-shape operation portion 26a and a thread portion 26b formed in the central portion of the operation portion 26a. As shown in the foregoing drawing, the second fixing screw 26 has the thread portion 26b which is screwed into the thread hole 14c and the thread hole 15c of the lower jaw model mount 15 through the bottom surface of the lower jaw model joining member 14 so as to secure the lower jaw model mount 15 to the upper surface of the mount joining portion 14a of the lower jaw model joining member 14.

The incisal table 16 is detachably combined with the table joining groove 14b formed at the leading end of the lower jaw model joining member 14. The incisal table 16 incorporates a base 16a on which a fore-and-aft engaging projection arranged to be engaged to the table joining groove 14b is formed on the side surface thereof; and a table 16b integrally formed with the leading end of the base 16a. The table 16b has a main surface formed into an inclined surface in the forward direction. As described later, a V-like shape receiving groove 16c against which the leading end of the mounting plaster 2 is abutted is provided for the table 16b. Since the angle of opening of the receiving groove 16c varies depending on the shape of the lower jaw of each patient, an incisal table 16 having an adaptable angle is selected and joined to the lower jaw model joining member 14. The incisal table 16 can be changed such that it is inserted/removed to and from the table joining groove 14b from the leading end of the lower jaw model joining member 14.

Figure 8:
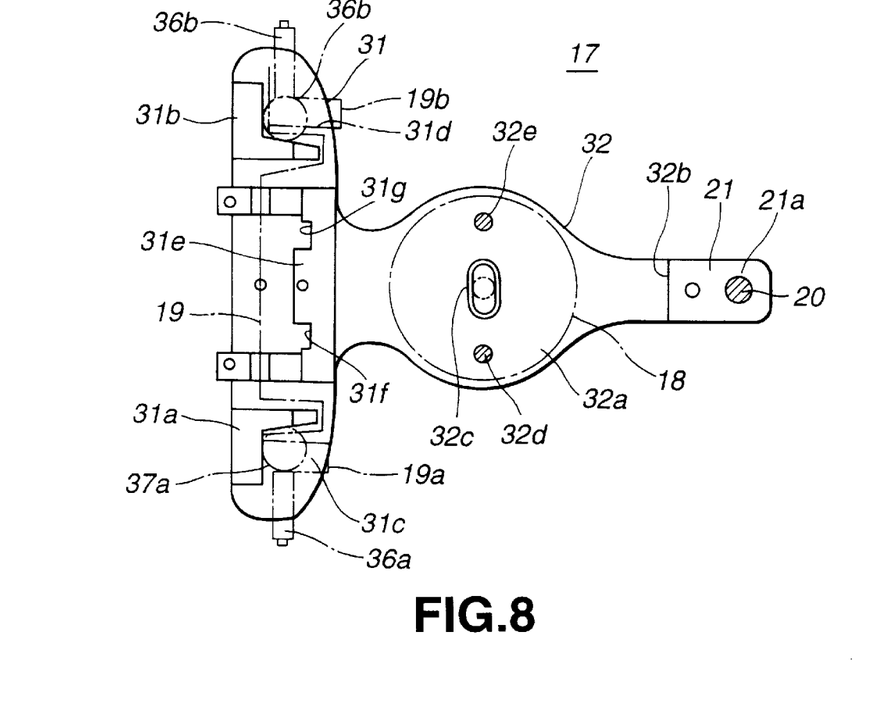
FIG. 8 is a bottom view showing the structure of an upper jaw model joining member constituting the articulator.

The upper jaw model joining member 17 incorporates: a base 31 made of, for example, aluminum die-cast or stainless steel and formed integrally and disposed opposite to the stand 13; and an upper jaw joining portion 32 forwards and integrally formed from the central portion of the base 31 in a direction in parallel with the lower jaw model joining member 14. That is, the upper jaw model joining member 17 is formed into a T-like shape. As shown in FIG. 8, the upper jaw model joining member 17 has engaging grooves 31c and 31d which are formed on the lengthwise directional two sides of the bottom surface of the base 31 and which have side and front surfaces opened by engaging projections 31a and 31b which constitute the rotation support mechanism 22. Each of the engaging grooves 31c and 31d has a circular arc bottom surface (not shown). The upper jaw model joining member 17 has a leaf-spring joining portion 31e which is formed at the center of the base 31 and to which the leaf spring 19 is joined. The upper jaw model joining member 17 has coil joining portions 31f and 31g which are formed on the two sides of the leaf-spring joining portion 31e and to which coil springs (not shown) are joined.

The articulator 10 has the base 31 structured as described above and formed such that the leaf spring 19 is joined to the leaf-spring joining portion 31e. The leaf spring 19 has engaging members 19a and 19b integrally formed at two ends thereof to project forwards so that the leaf spring 19 has a bent and crank-like shape. The leaf spring 19 is joined to the upper jaw model joining member 17 so that the leaf spring 19 constitutes the bottom surfaces of the engaging grooves 31c and 31d. The engaging members 19a and 19b of the leaf spring 19 are urged in a direction in which the widths of the engaging grooves 31c and 31d are enlarged by coil springs (not shown) received by the coil joining portions 31f and 31g. The engaging members 19a and 19b of the leaf spring 19 are pressed in a direction in which the widths of the engaging grooves 31c and 31d are reduced against the elastic force of a coil spring by dint of a locking member (not shown) rotatively joined to the base 31.

The central portion of the upper jaw joining portion 32 is formed into a mount joining portion 32a to which the upper jaw model mount 18, to be described later is joined. The mount joining portion 32a is formed into a circular arc shape expanding toward the two sides. A joining portion 32b, to which the incisal pin holder 21 to be described later is joined, is formed at the leading end of the upper jaw joining portion 32. The mount joining portion 32a of the upper jaw joining portion 32 has an elongated hole 32c formed at the center thereof, the elongated hole 32c being formed in a right and left direction so that the upper jaw model mount 18 is joined to the elongated hole 32c. A pair of engaging pins 32d and 32e are stood erect such that the elongated hole 32c is interposed between the engaging pins 32d and 32e. The upper jaw model mount 18 is joined to the upper surface of the mount joining portion 32a of the upper jaw joining portion 32.

Figure 9:
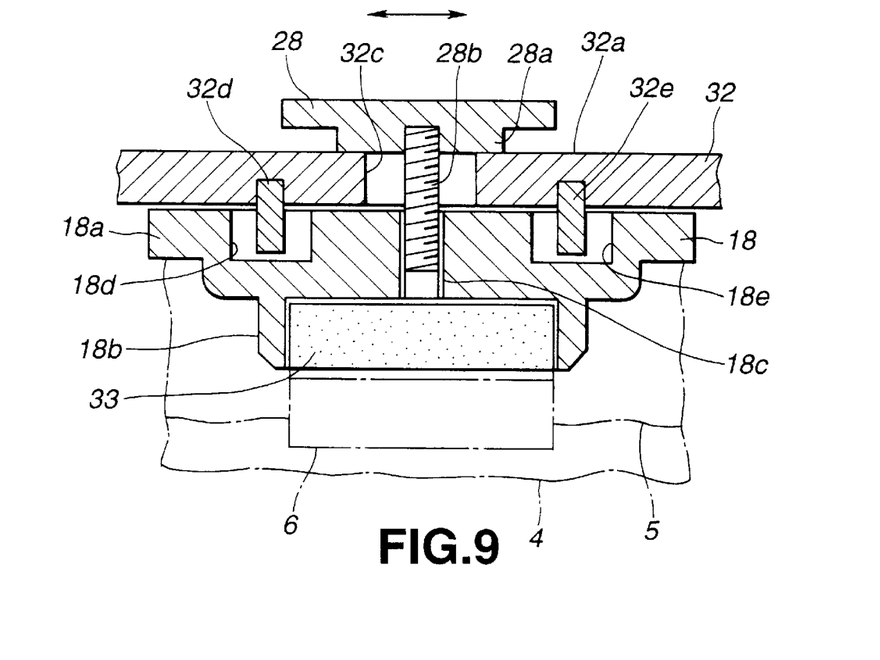
FIG. 9 is a vertical cross sectional view showing an essential portion of the structure formed by combining the upper jaw model joining member and an upper jaw model mount which constitute the articulator.

As shown in FIGS. 1 to 3, the upper jaw model 4 is mounted on the upper jaw model mount 18 through mounting plaster 5 and a metal plate 6. As shown in FIG. 9, the upper jaw model mount 18 incorporates a disc-like base 18a and an annular projection 18b integrally projecting over the main surface of the base 18a. The base 18a has, at the center thereof, a thread hole 18c which penetrates the annular projection 18b. A disc-shape magnet plate 33 for magnetically chucking the metal plate 6 of the upper jaw model 4 is joined to the inside portion of the annular projection 18b. The upper jaw model mount 18 has elongated grooves 18d and 18e which are configured horizontally such that the thread hole 18c is interposed between the elongated grooves 18d and 18e. In a state in which the upper jaw model mount 18 has been combined with the upper jaw model joining member 17, the engaging pins 32d and 32e stood erect on the upper jaw model mount 18 are engaged to the elongated grooves 18d and 18e.

As described above, the upper jaw model mount 18 is secured to the upper surface of the mount joining portion 32a of the upper jaw model joining member 17 by the fourth fixing screw 28 such that the horizontal direction of the upper jaw model mount 18 can be adjusted. As shown in FIG. 9, the fourth fixing screw 28 incorporates a disc-shape operation portion 28a and a thread portion 28b formed at the center of the operation portion 28a. When the thread portion 28b of the fourth fixing screw 28 is screwed in the thread hole 18c of the upper jaw model mount 18 through the elongated hole 32c from the upper surface of the upper jaw joining portion 32 as shown in FIG. 9, the fourth fixing screw 28 secures the upper jaw model mount 18 to the upper surface of the mount joining portion 32a of the upper jaw model joining member 17. The horizontal position of the upper jaw model mount 18 is adjusted within a range of the length of the elongated hole 32c of the upper jaw joining portion 32 as indicated by an arrow shown in FIG. 9. Moreover, the rotation of the upper jaw model mount 18 is inhibited by the engaging pins 32d and 32e, which are engaged to the elongated grooves 18d and 18e.

The upper jaw model joining member 17 structured as described above is combined with the upper portion of the stand 13, which constitutes the lower jaw frame 11 by the rotation support mechanism 22 and the slide support mechanism 23, such that the upper jaw model joining member 17 is able to move in the vertical and fore-and-aft directions. The rotation support mechanism 22 incorporates a pair of right and left bearing members 35 (35a and 35b), support shafts 36 (36a and 36b) and articulation bearing members 37 (37a and 37b). The slide support mechanism 23 incorporates a bearing member 35 and a pair of right and left slide shafts 34 (34a and 34b). As described above, the rotation support mechanism 22 rotatively supports the upper jaw model joining member 17 within a predetermined angular range with respect to the stand 13. Moreover, the rotation support mechanism 22 makes the upper jaw model joining member 17 to be detachable from the stand 13. The slide support mechanism 23 enables the height of the upper jaw model joining member 17 to be adjustable with respect to the stand 13.

Figure 11:
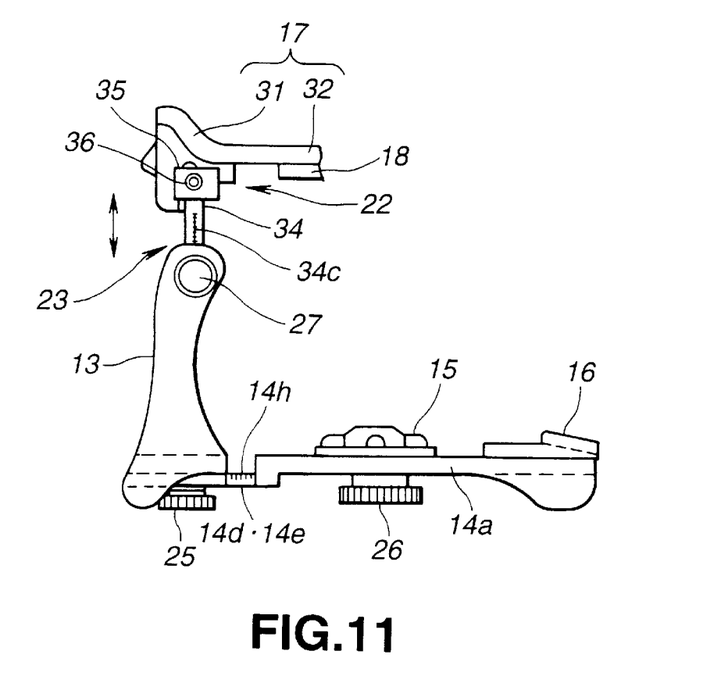
FIG. 11 is a side view showing an essential portion of the operation of the slide support mechanism of the articulator for adjusting the height of the upper jaw model joining member with respect to the stand in a state in which the upper jaw model joining member has been slid upwards.

The lower ends of the slide shafts 34 are movably inserted into the slide guide openings 13f and 13g formed in the columnar portions 13a and 13b of the stand 13. The upper ends of the slide shafts 34 are secured to the bearing members 35. As shown in FIG. 11, the slide shafts 34 have indexes 34c for indicating an amount of slid when the height of the upper jaw model joining member 17 is adjusted with respect to the stand 13 as described later.

Each of the bearing members 35 has a horizontal shaft hole (not shown). The support shafts 36 are rotatively inserted into the shaft holes. Spherical articulation bearing members 37 are integrally formed with the leading end of each of the support shafts 36. As shown in FIG. 8, the articulation bearing members 37 are engaged to engaging grooves 31c and 31d of the base 31 of the upper jaw model joining member 17. When the articulation bearing members 37 are engaged to the engaging grooves 31c and 31d, the articulation bearing members 37 are pressed against the bottom surfaces of the engaging grooves 31c and 31d by the engaging members 19a and 19b of the leaf spring 19 pressed in a direction in which the widths of the engaging grooves 31c and 31d are reduced by the locking member (not shown). The articulation bearing members 37 correspond to the jaw joints of the patient.

The articulator 10 is provided with the rotation support mechanism 22 having the above-mentioned elements. Thus, when the upper jaw model 4 is joined to the upper jaw model joining member 17 or when the upper jaw model 4 or the lower jaw model 1 is adjusted, the rotation support mechanism 22 enables the upper jaw model joining member 17 to be rotated with respect to the stand 13, as shown in FIG. 3. In a state where the upper jaw model joining member 17 has been rotated with respect to the stand 13 of the articulator 10, the lock suspending operation of the locking member (not shown) to suspend the state in which the widths of the engaging members 19a and 19b of the leaf spring 19 are reduced is performed. Thus, the articulation bearing members 37 can be removed from the engaging grooves 31c and 31d. Thus, the upper jaw model joining member 17 of the articulator 10 is removed from the stand 13 in a direction indicated by an arrow shown in the drawing.

Figure 10:
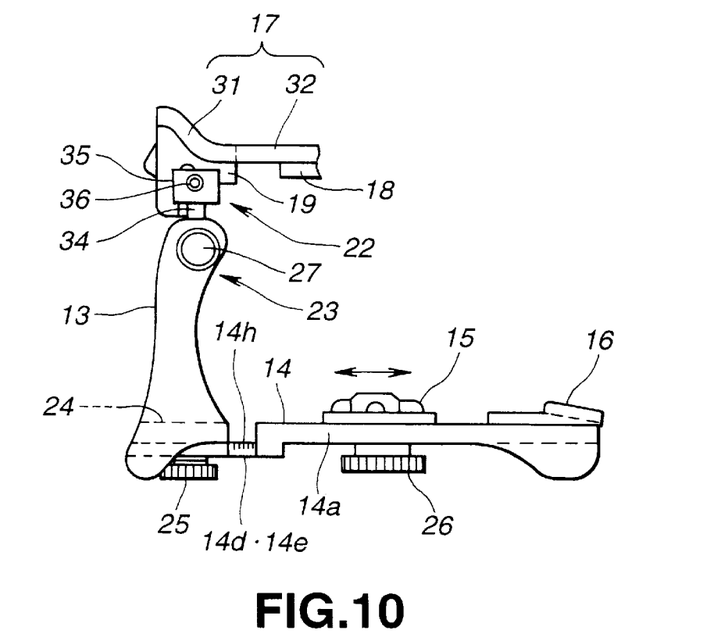
FIG. 10 is a side view showing an essential portion of the operation of the slide support mechanism of the articulator for adjusting the height of the upper jaw model joining member with respect to the stand in a state in which the upper jaw model joining member is brought to the lowermost position.

The articulator 10 is provided with the slide support mechanism 23 incorporating the above-mentioned elements. Thus, the upper jaw model joining member 17 is vertically slid with respect to the stand 13 so that the occlusion height between the lower jaw model 1 and the upper jaw model 4 is adjusted or the occlusion in the horizontal direction is adjusted. That is, the state of the articulator 10 shown in FIG. 10 is brought to a state in which the third fixing screw 27 is loosened so that the locking state of the slide shafts 34 in the slide guide openings 13f and 13g is suspended. In the above-mentioned state, the index 34c of the articulator 10 is used so that the upper jaw model joining member 17 is moved upwards with respect to the stand 13. In the state of the articulator 10 in which the upper jaw model joining member 17 has been moved upwards to a predetermined height with respect to the stand 13, the third fixing screw 27 is tightened so that the upper jaw model joining member 17 is set to be a predetermined height, as shown in FIG. 11. As a result of the above-mentioned operation of the articulator 10, the height of the occlusion of the patient can be reproduced. Thus, the height of the occlusion between the lower jaw model 1 and the upper jaw model 4 can be adjusted.

The height of the upper jaw model joining member 17 of the articulator 10 with respect to the stand 13 is performed independently by the slide support mechanisms 23a and 23b configured horizontally. Thus, the heights of the right- and left-hand portions of the upper jaw model joining member 17 with respect to the stand 13 of the articulator 10 are independently adjusted. As a result of the above-mentioned operation, the right and left occlusion states of the patient can be realized by the articulator 10. Thus, the right and left occlusion of the lower jaw model 1 and the upper jaw model 4 can be adjusted.

When the height of the upper jaw model joining member 17 with respect to the stand 13 is adjusted, the articulator 10 is able to adjust the upper jaw model joining member 17 in the fore-and-aft direction. The slide shafts 34 of the articulator 10 is movably inserted into the slide guide openings 13f and 13g of the stand 13. When the third fixing screw 27 of the articulator 10 is loosened, the slide shafts 34 are able to rotate in the slide guide openings 13f and 13g. When the slide shafts 34 of the articulator 10 have been rotated, the upper jaw model joining member 17 can be adjusted in the fore-and-aft direction through the articulation bearing members 37.

The articulation bearing members 37 are elements corresponding to the condyle. Conventional articulators, which are capable of adjusting the articulation bearing members 37 in the vertical direction, cannot adjust the fore-and-aft direction. Since the condyle performs the movements in the fore-and-aft direction, the articulator 10 is structured such that the adjustment of the articulation bearing members 37 corresponding to the condyle in the fore-and-aft direction can be performed. Thus, the complicated occlusion motions of the upper and lower jaws of the patient can furthermore precisely be reproduced.

Figure 12:
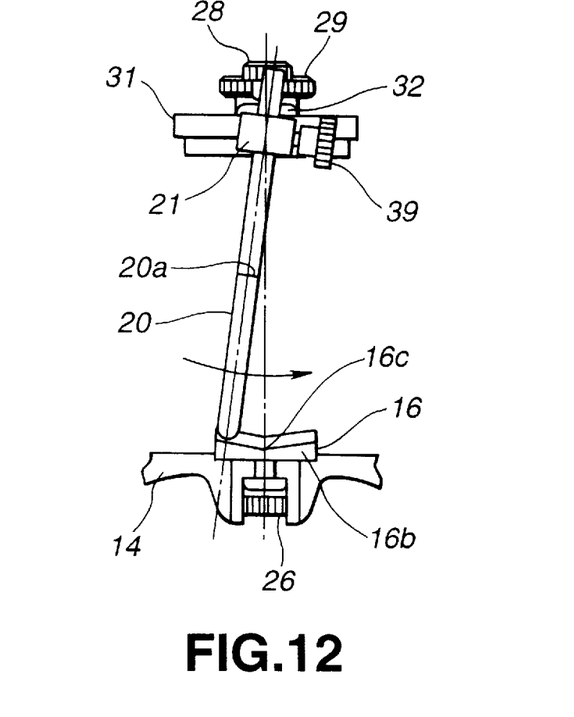
FIG. 12 is a front view showing an essential portion of the operation of an incisal pin for adjusting the angle of the articulator.
Figure 13:
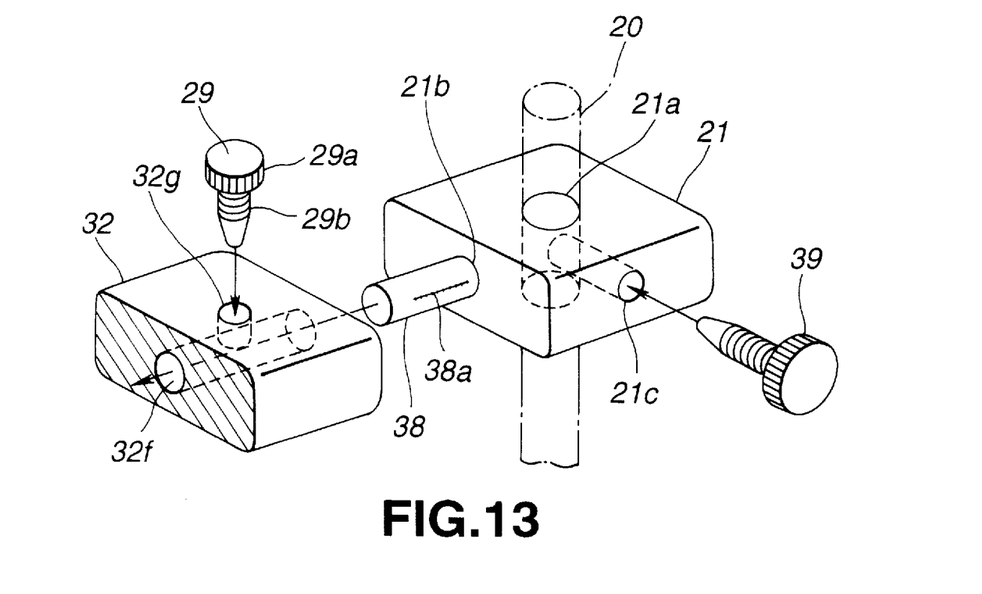
FIG. 13 is an exploded perspective view showing a support structure of the incisal pin.

The slide support mechanisms 23a and 23b of the articulator 10 configured horizontally are independently adjusted, the upper jaw model joining member 17 is inclined and thus the perpendicularity of the incisal pin 20 cannot be maintained. As shown in FIGS. 12 and 13, the articulator 10 is provided with a mechanism for adjusting the angle of the incisal pin 20. The angle adjustment mechanism incorporates the joining portion 32b formed at the leading end of the mount joining portion 32a and the incisal pin holder 21 joined to the joining portion 32b. That is, the joining portion 32b has a horizontal joining hole 32f opened at the front end thereof, as shown in FIG. 13. Moreover, the joining portion 32b has a thread hole 32g which is allowed to communicate with the joining hole 32f. As shown in FIG. 13, the thread portion 29b of the fifth fixing screw 29, incorporating the disc-shape operation portion 29a and the thread portion 29b formed at the center of the operation portion 29a, is screwed in the thread hole 32g.

The incisal pin holder 21 has a rectangular shape having a thickness which is substantially the same as that of the joining portion 32b. Moreover, the overall outer edge of the incisal pin holder 21 is chamfered. The incisal pin holder 21 has an incisal-pin joining hole 21a which penetrates the upper and lower main surfaces thereof. The incisal pin holder 21 has a horizontal joining hole 21b opened in the surface opposite to the joining portion 32b. The incisal pin holder 21 has a thread hole 21c which is formed in the side surface thereof and which is allowed to communicate with the incisal-pin joining hole 21a. The incisal pin 20 penetrates the incisal-pin joining hole 21a of the incisal pin holder 21 so that the incisal pin holder 21 is supported. A connection shaft 38 having a leading end which projects over the joining hole 21b is engaged to the incisal pin holder 21. A fixing screw 39 is screwed in the thread hole 21c of the incisal pin holder 21.

When the connection shaft 38 is inserted into the joining hole 32f of the joining portion 32b, the incisal pin holder 21 is combined with the upper jaw model joining member 17 such that the incisal pin holder 21 is able to rotate and slide in the fore-and-aft direction. Since the connection shaft 38 is secured by the fifth fixing screw 29 screwed in the thread hole 32g, the incisal pin holder 21 is secured to the leading end of the joining portion 32b of the upper jaw model joining member 17. Note that the connection shaft 38 has an index 38a for indicating an amount of projection of the incisal pin bolder 21 with respect to the joining portion 32b, as shown in FIG. 13.

The incisal pin 20 has an inscribed index 20a at the center in the direction of the height. As shown in FIG. 1, the incisal pin 20 is supported by the incisal pin holder 21 such that the leading end of the incisal pin 20 is abutted against the receiving groove 16c of the incisal table 16. As described above, the incisal pin 20 is inserted into the incisal-pin joining hole 21a and secured by the fixing screw 39 which is screwed in the thread hole 21c. Since the right- and left-hand directional heights of the upper jaw model joining member 17 with respect to the stand 13 are independently adjusted through the slide support mechanism 23, displacements of the incisal pin 20 in the right and left directions with respect to the incisal table 16 must be adjusted in addition to the adjustment of the height.

That is, the upper jaw model joining member 17 is adjusted with respect to the stand 13 of the articulator 10 such that the right- and left-hand heights are independently adjusted. Thus, as shown in FIG. 12, the incisal pin 20 is abutted against the incisal table 16 such that the incisal pin 20 is somewhat inclined. The angle adjustment mechanism of the articulator 10 adjusts the inclination of the incisal pin 20. The fifth fixing screw 29 of the articulator 10 is loosened to rotate the incisal pin holder 21 with respect to the upper jaw model joining member 17 such that the connection shaft 38 serves as a fulcrum. Thus, the incisal pin 20 is abutted against the receiving groove 16c of the incisal table 16. Then, the fifth fixing screw 29 of the articulator 10 is tightened so that the incisal pin holder 21 is secured to the upper jaw model joining member 17. Thus, a state in which the incisal pin 20 is abutted against the receiving groove 16c of the incisal table 16 is maintained.

On the other hand, the articulator 10 has the structure that the lower jaw model joining member 14 is slid with respect to the stand 13 through the slide guide mechanism 24. Thus, the occlusion between the lower jaw model 1 and the upper jaw model 4 in the fore-and-aft direction is adjusted. When the articulation bearing members 37 of the articulator 10 have been rotated, the upper jaw model joining member 17 is moved with respect to the lower jaw model joining member 14 so as to be adjusted. Thus, the occlusion between the lower jaw model 1 and the upper jaw model 4 in the fore-and-aft direction is adjusted. In the articulator 10, the above-mentioned adjustment causes the relative position between the incisal table 16 and the incisal pin 20 to be changed. When the fifth fixing screw 29 of the articulator 10 is loosened, the incisal pin holder 21 is removed from the upper jaw model joining member 17 through the connection shaft 38 such that the index 38a is used. Then, the fifth fixing screw 29 of the articulator 10 is tightened so that the position of the incisal pin 20 in the fore-and-aft direction is set.

A process for joining the lower jaw model 1 and the upper jaw model 4 of the articulator 10 having the above-mentioned structure and a method of adjusting the occlusion between the lower jaw model 1 and the upper jaw model 4 will now be described. Note that the adjustment of the occlusion between the lower jaw model 1 and the upper jaw model 4 is a process for reproducing the positions of the elements of the articulator 10 to correspond to the shape of the jaws of the patient. The adjustment or correction is performed such that the lower jaw model 1 and the upper jaw model 4 are normally occluded with each other in a 3D direction with reference to the reproduced elements. In the articulator 10, the upper jaw model 4 is mounted on the main surface of the upper jaw model mount 18 as described above. As shown in FIG. 1, the upper jaw model 4 is structured such that the thickness of the bonding plaster 5 is adjusted while the position of the occlusion is aligned to the index 20a of the incisal pin 20. Moreover, the metal plate 6 is embedded in the bonding plaster 5. When the metal plate 6 is magnetically chucked to the magnet plate 33, the upper jaw model 4 is mounted on the upper jaw model mount 18.

In the articulator 10, the upper jaw model mount 18 on which the upper jaw model 4 has been mounted is adjusted in the horizontal direction within the range of the length of the elongated hole 32c to correspond to the state of the upper jaw model 4 so that the upper jaw model mount 18 is located. Then, the fourth fixing screw 28 is tightened so that the upper jaw model 4 is secured to the main surface of the upper jaw joining portion 32 of the upper jaw model joining member 17. In the articulator 10, the lower jaw model 1 is mounted on the main surface of the lower jaw model mount 15. The thickness of the mounting plaster 2 of the lower jaw model 1 is adjusted in such a manner that the position of the occlusion is aligned to the index 20a of the incisal pin 20. Moreover, the metal plate 3 is embedded in the mounting plaster 2. When the metal plate 3 is magnetically chucked to the magnet plate 30, the lower jaw model 1 is mounted on the lower jaw model mount 15.

In the articulator 10, the height of the occlusion between the lower jaw model 1 and the upper jaw model 4 is adjusted by operating the slide support mechanism 23. Moreover, the height of the incisal pin 20 is adjusted. In the articulator 10, the slide support mechanisms 23a and 23b configured horizontally are independently operated so that the right- and left-hand heights of the occlusion between the lower jaw model 1 and the upper jaw model 4 are adjusted. The inclination of the incisal pin 20 of the articulator 10 is adjusted by rotating the incisal pin holder 21. In the articulator 10, the occlusion between the lower jaw model 1 and the upper jaw model 4 in the fore-and-aft direction is adjusted by operating the slide guide mechanism 24.

Figure 14:
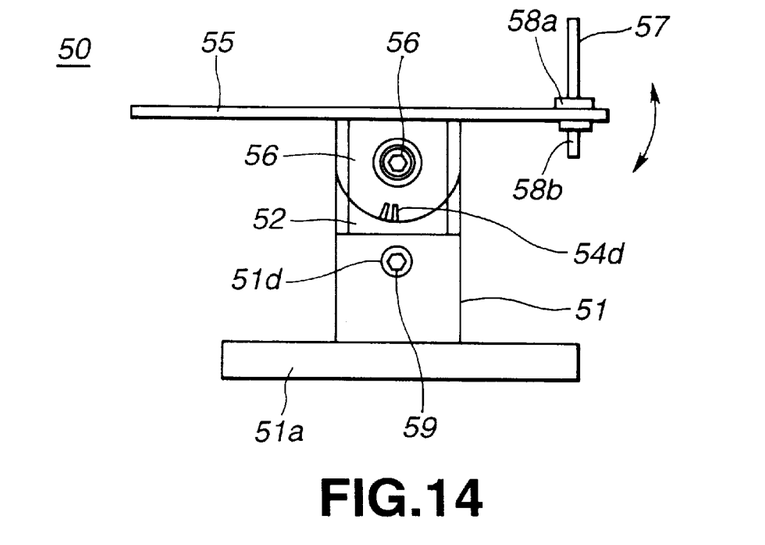
FIG. 14 is a side view showing a model joining adjustment apparatus of the articulator which constitutes a basic jig for mounting the upper jaw on the upper jaw model joining member.
Figure 15:
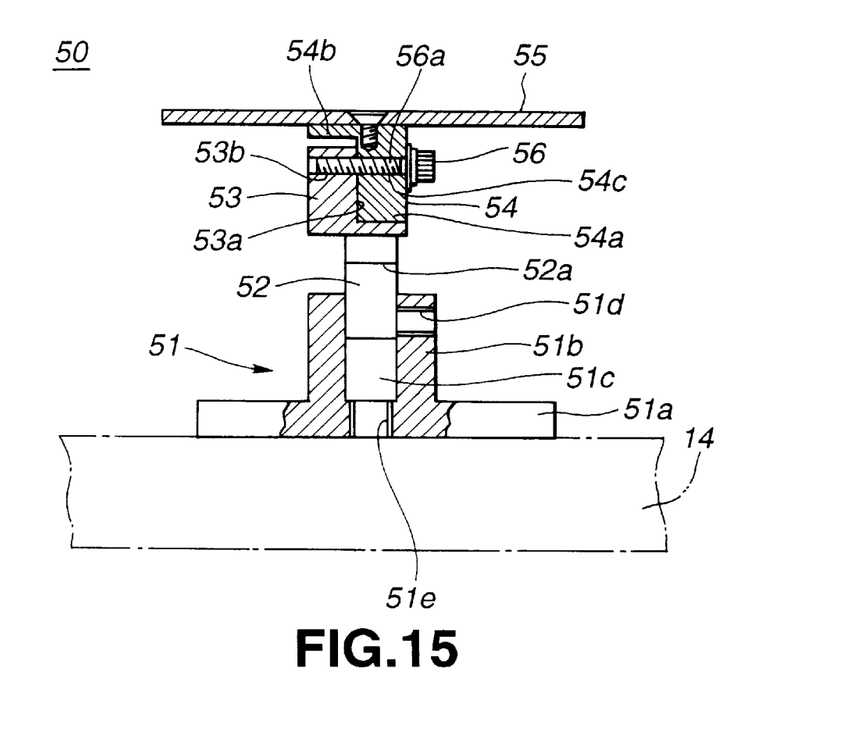
FIG. 15 is a vertical cross sectional view showing the model joining adjustment apparatus.

The lower jaw model 1 and the upper jaw model 4 are manufactured by using the articulator 10 such that the lower jaw model 1 is adjusted and corrected with reference to the upper jaw model 4 mounted on the upper jaw model joining member 17. A model joining adjustment apparatus 50 is used together with the articulator 10 in order to accurately mounting the upper jaw model 4 on the upper jaw model joining member 17. As shown in FIGS. 14 and 15, the model joining adjustment apparatus 50 incorporates a base 51, a connection shaft 52, a support member 53, a rotative member 54, an upper-jaw-model joining reference frame 55 and so forth.

The base 51 incorporates a disc-shape base 51a and a cylindrical support portion 51b stood erect at the center of the base 51a and provided with a joining hole 51c opened at an upper end thereof. The joining hole 51c penetrates the base 51a. A bush 51e is fit to the lower end of the joining hole 51c. The support portion 51b has a thread hole 51d which is allowed to communicate with the joining hole 51c. The connection shaft 52 has a lower end which is inserted into the joining hole 51c and an upper end with which a support member 53 is integrally formed. The connection shaft 52 has an index 52a for indicating the height of the occlusion, the index 52a being arranged to correspond to the index 20a of the incisal pin 20. The connection shaft 52 is secured to the base 51 by a stopper screw 59 which is screwed in the thread hole 51d. When the stopper screw 59 is loosened, the connection shaft 52 is slid in the joining hole 51c so that the height of the upper-jaw-model joining reference frame 55 is adjusted.

As shown in FIG. 15, a space 53a is formed in the support member 53 by cutting so that the cross section of the support member 53 is formed into an L-like shape. The support member 53 has a horizontal thread hole 53b formed in the space 53a thereof. The rotative member 54 incorporates a fulcrum 54a having a thickness which is substantially the same as that of the space 53a of the support member 53. Moreover, the rotative member 54 incorporates a horizontal joining portion 54b, integrally formed with the upper end of the fulcrum 54a and having a semi-circular shape. The rotative member 54 has a through hole 54c which is allowed to communicate with the thread hole 53b in a state in which the fulcrum 54a is superimposed on the space 53a so as to be combined with the support member 53.

The rotative member 54 is provided with an index 54d for indicating an amount of rotation, the index 54d being provided for the side surface of the rotative member 54. The rotative member 54 is secured such that the fulcrum 54a is secured to the support member 53 by dint of the fixing screw 56 having the thread portion 56a screwed in the thread hole 53b through the through hole 54c. When the fixing screw 56 is loosened, the rotative member 54 is rotated by a predetermined angular degree with respect to the support member 53 such that the index 54d is used.

The upper-jaw-model joining reference frame 55 has a rectangular plate-like shape. The upper-jaw-model joining reference frame 55 is superimposed on the joining portion 54b of the rotative member 54 and secured with a screw. The rotative member 54 has a fore-and-aft slit (not shown) which is formed at a center of the leading end thereof and to which a positioning pin 57 is joined. The positioning pin 57 is a member for defining the central position (a median suture) of the upper jaw model 4. As shown in FIG. 14, the positioning pin 57 is secured by tightening a pair of fixing screws 58a and 58b disposed vertically when the positioning pin 57 is slid in the fore-and-aft direction along the slit.

Figure 16:
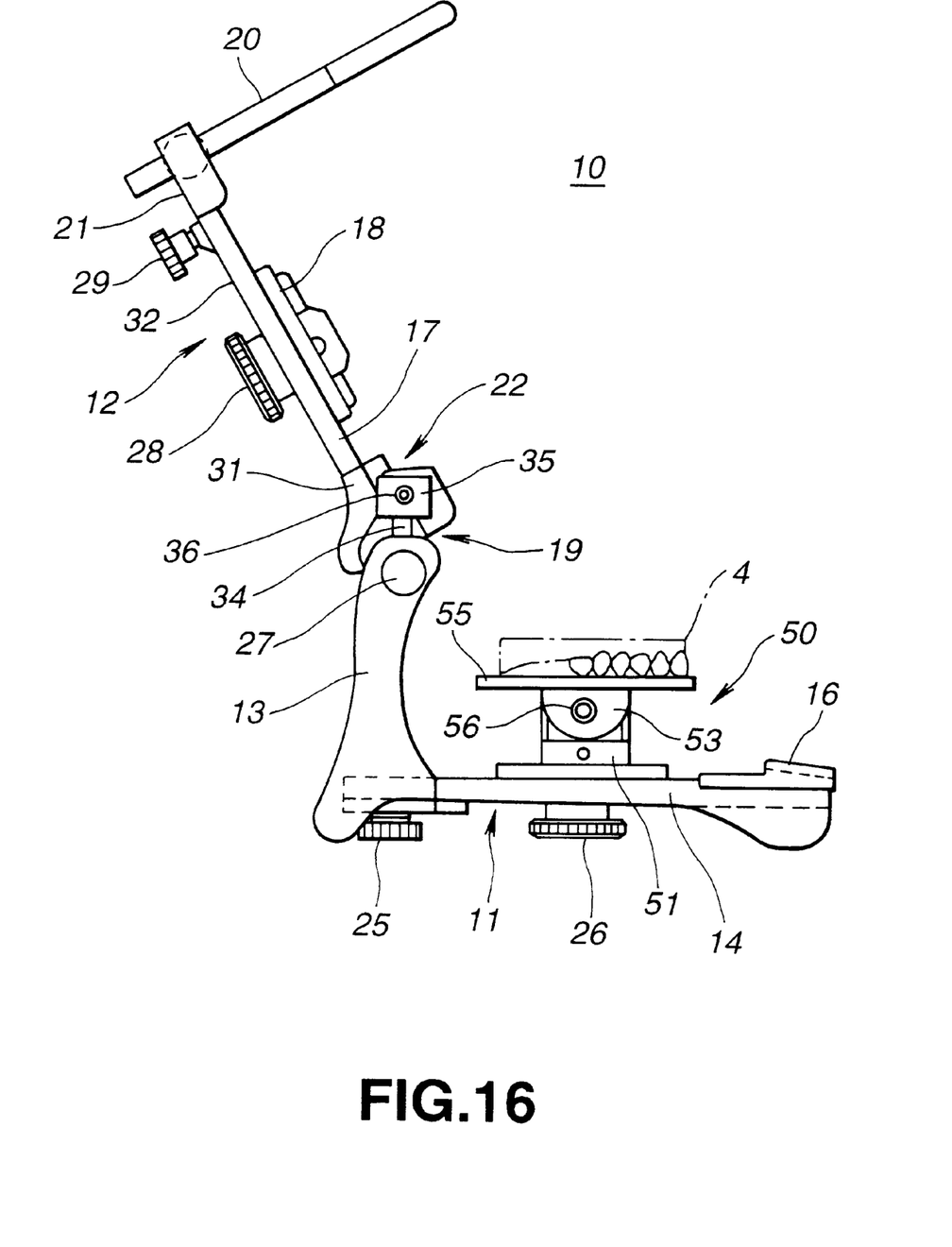
FIG. 16 is a diagram showing a state in which the model joining adjustment apparatus has been joined to the articulator and the upper jaw model has been located by the model joining adjustment apparatus.

The model joining adjustment apparatus 50 having the above-mentioned structure is, as shown in FIG. 16, joined to the upper surface of the lower jaw model joining member 14 of the articulator 10, from which the lower jaw model mount 15 has been removed. The model joining adjustment apparatus 50 is adjusted by the second fixing screw 26. The height of the model joining adjustment apparatus 50 is adjusted such that the index 52a of the connection shaft 52 is aligned to the index 20a of the incisal pin 20. As a result of the foregoing operation, the height of the upper-jaw-model joining reference frame 55 of the model joining adjustment apparatus 50 is adjusted with respect to the Frankfort plane. When the fixing screw 56 is loosened, the rotative member 54 of the model joining adjustment apparatus 50 is rotated by a predetermined angular degree with respect to the support member 53. Thus, the inclination of the upper-jaw-model joining reference frame 55 is set to correspond to the inclination of the occlusion surface with respect to the Frankfort plane of the patient. The upper jaw model 4 is temporarily joined to the main surface of the upper-jaw-model joining reference frame 55 of the model joining adjustment apparatus 50, as shown in FIG. 16.

Figure 17:
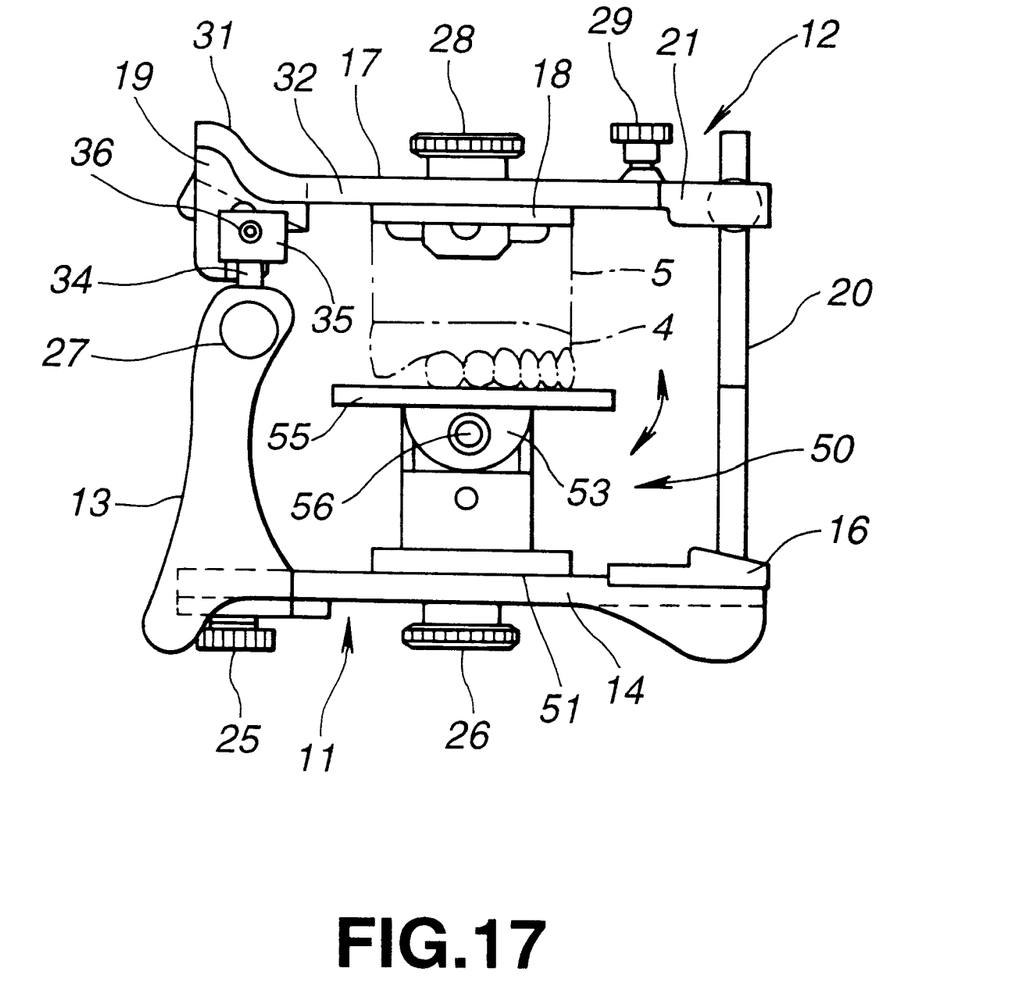
FIG. 17 is a diagram showing the operation for joining the upper jaw model located by the model joining adjustment apparatus on the upper jaw model joining member.

The center of the upper jaw model 4 is located through the positioning pin 57 when the upper jaw model 4 is temporarily joined. As shown in FIG. 17, the bonding plaster 5, for plugging the space from the upper jaw model mount 18, is added to the upper jaw model 4 and then the upper jaw model 4 is secured to the upper jaw model mount 18. Note that the metal plate 6 is embedded in the bonding plaster 5. The upper jaw model 4 secured to the upper jaw model mount 18 is removed from the upper-jaw-model joining reference frame 55 of the model joining adjustment apparatus 50.

The lower jaw model mount 15 is joined to the lower jaw model joining member 14 of the articulator 10 by the second fixing screw 26. Moreover, the lower jaw model 1 is mounted on the lower jaw model mount 15 through the mounting plaster 2 and the metal plate 3. In the articulator 10, the lower jaw model 1 is joined to the lower jaw model joining member 14 with reference to the upper jaw model 4 located and joined to the upper jaw model joining member 17. As a matter of course, the articulator 10 may be structured such that the model joining adjustment apparatus 50 is not used to mount the lower jaw model 1 and the upper jaw model 4.

The above-mentioned model joining adjustment apparatus 50 incorporates the connection shaft 52, the support member 53 and the rotative member 54, which are disposed between the base 51 and the upper-jaw-model joining reference frame 55 in order to adjust the height and the angle. The present invention is not limited to the above-mentioned structure. For example, the model joining adjustment apparatus 50 may have a mechanism for adjusting the angle of the upper-jaw-model joining reference frame 55 such that the upper-jaw-model joining reference frame 55 is directly and rotatively joined to the base 51.

As described above, the articulator according to the present invention has the following structure: the upper jaw model mount is joined such that the horizontal direction with respect to the upper jaw model joining member can be adjusted; the upper jaw model joining member is joined such that the right- and left-hand directional heights with respect to the stand can independently be adjusted; the lower jaw model joining member is joined such that the fore-and-aft direction with respect to the stand can be adjusted; and the incisal pin is joined such that the rotational direction and the height with respect to the upper jaw model joining member can be adjusted. Thus, the adjustment in each direction can independently be performed so as to precisely reproduce the shape of the jaws of a patient. Therefore, the structure can be simplified and adjustment can easily be performed. As a result, a precise upper jaw model and a lower jaw model can efficiently be manufactured. Since the articulator according to the present invention has the structure that the each adjustment portion is not provided for the mount of the lower jaw model, the adjustment should not be hampered because of adhesion of rust and/or plaster. Therefore, maintenance can easily be performed and easy handling is permitted.

Since the articulator is provided with the model joining adjustment apparatus arranged to be joined to the upper jaw model joining member, the upper jaw model can accurately be mounted on the upper jaw model mount. Therefore, a precise upper jaw model and a lower jaw model can efficiently be manufactured.

Although the invention has been described in its preferred form with a certain degree of particularity, it is understood that the present disclosure of the preferred form can be changed in the details of construction and in the combination and arrangement of parts without departing from the spirit and the scope of the invention as hereinafter claimed.

What is claimed is:

1. An articulator comprising:
a lower jaw frame comprising a stand constituted by a pair of columnar portions and a connection portion for connecting said columnar portions to each other such that said columnar portions and said connection portion are integrally formed, a lower jaw model joining member combined such that a base portion of said lower jaw model joining member is slidable in a horizontal direction with respect to said connection portion of said stand, a lower jaw model mount which is joined to a joining portion at the center of a main surface of said lower jaw model joining member and which has a main surface on which a lower jaw model is mounted, and an incisal table provided for another end of said lower jaw model joining member; and an upper jaw frame incorporating an upper jaw model joining member having side portions of a base portion which are supported by a rotation support mechanism and a slide support mechanism such that the side portions are rotative and slidable with respect to each columnar portion of said stand, an upper jaw model mount which corresponds to said lower jaw model mount, which is joined to a joining portion formed at the center of a main surface of said upper jaw model joining member constituting a Frankfort plane and which is movable in a horizontal direction perpendicular to a sliding direction of said lower jaw model joining member, and an incisal pin joined to a leading end of said upper jaw model joining member through a support mechanism which is slidably supported such that oscillations are permitted in said leading end of said upper jaw model joining member.

2. An articulator according to claim 1, wherein each element of said upper jaw frame and lower jaw frame is chamfered so that the outer edge of each element is formed into a circular arc shape.

3. An articulator according to claim 2, wherein said upper jaw model joining member is joined such that the right- and left-hand directional heights with respect to said stand can independently be adjusted.

4. An articulator according to claim 2, wherein said incisal pin is joined such that the rotational direction and the height with respect to said upper jaw model joining member can be independently adjusted.

5. An articulator according to claim 1, wherein said upper jaw model joining member is joined such that the right- and left-hand directional heights with respect to said stand can independently be adjusted.

6. An articulator according to claim 1, wherein said incisal pin is joined such that the rotational direction and the height with respect to said upper jaw model joining member can be independently adjusted.

* * * * *